US012630861B2

(12) United States Patent
Qu et al.

(10) Patent No.: US 12,630,861 B2
(45) Date of Patent: May 19, 2026

(54) PROTECTION METHOD, PROTECTION SEQUENCE, COMPOSITION AND KIT FOR PREVENTING RNA DEGRADATION, AND USE THEREOF

(71) Applicants: THE EYE HOSPITAL OF WENZHOU MEDICAL UNIVERSITY, Wenzhou City (CN); HANZHOU BAISAISI BIOTECHNOLOGY CO., LTD., Hangzhou City (CN); WENZHOU OJA BIOTECHNOLOGY CO., LTD., Wenzhou City (CN)

(72) Inventors: Jia Qu, Wenzhou City (CN); Tao Xu, Wenzhou City (CN); Jingu Wang, Wenzhou City (CN); Jiangfan Chen, Wenzhou City (CN); Liangde Xu, Wenzhou City (CN)

(73) Assignee: The Eye Hospital of Wenzhou Medical University, Wenzhou City (CN)

( * ) Notice: Subject to any disclaimer, the term of this patent is extended or adjusted under 35 U.S.C. 154(b) by 363 days.

(21) Appl. No.: 18/003,456

(22) PCT Filed: Aug. 31, 2020

(86) PCT No.: PCT/CN2020/112399
§ 371 (c)(1),
(2) Date: Dec. 27, 2022

(87) PCT Pub. No.: WO2022/000753
PCT Pub. Date: Jan. 6, 2022

(65) Prior Publication Data
US 2024/0287576 A1 Aug. 29, 2024

(30) Foreign Application Priority Data
Jun. 28, 2020 (CN) .......................... 202010602226.4

(51) Int. Cl.
*C12Q 1/6806* (2018.01)

(52) U.S. Cl.
CPC .................................. *C12Q 1/6806* (2013.01)

(58) Field of Classification Search
CPC ...... C12Q 1/6806; C12Q 1/701; C12Q 1/686; C12Q 2600/16
See application file for complete search history.

(56) References Cited

U.S. PATENT DOCUMENTS

2016/0257950 A1    9/2016    Gong et al.

FOREIGN PATENT DOCUMENTS

| CN | 107406839 A | 11/2017 |
| CN | 109679946 A | 4/2019 |
| CN | 111020064 A | 4/2020 |
| CN | 111239392 A | 6/2020 |
| CN | 111635960 A | 9/2020 |
| WO | WO 2004/057016 A2 | 7/2004 |
| WO | WO 2004/094674 A1 | 11/2004 |

OTHER PUBLICATIONS

Paloske et al., Journal of Clinical Microbiology, vol. 36, No. 12, pp. 3590-3594, Dec. 1998.*
Xu et al., Brief Bioinformatics, pp. 1-20, Sep. 16, 2020.*
Jain, Chaitanya, "RNase AM, a 5' to 3' exonuclease, matures the 5' end of all three ribosomal RNAs in *E. coli*," *Nucleic Acids Research*, vol. 48, No. 10, pp. 5616-5623 (Apr. 28, 2020).
Bacharach, Eran, et al., "Deletion of a Short, Untranslated Region Adjacent to the Polypurine Tract in Moloney Murine Leukemia Virus Leads to Formation of Aberrant 5' Plus-Strand DNA Ends in Vivo," *Journal of Virology*, vol. 74, No. 10, pp. 4755-4764 (May 2000).
Xu, Tao, et al., "Identification of the RNase-binding site of SARS-CoV-2 RNA for anchor primer-PCR detection of viral loading in 306 COVID-19 patients," *Briefings in Bioinformatics*, vol. 22, No. 2, pp. 1215-1224 (2021).

* cited by examiner

*Primary Examiner* — Cynthia B Wilder
(74) *Attorney, Agent, or Firm* — Christensen, Fonder, Dardi & Herbert PLLC; John P. Fonder

(57) ABSTRACT

A protection method, a protection sequence, a composition and a kit for preventing RNA degradation, and the use thereof, which can improve the protective effect on viral RNA. After the protection sequence RNase AP is added, the three-dimensional structure of RNA and the structural allosteric characteristics of RNA can be protected; and the protection sequence has a good protection effect on RNA integrity, and a high-level detection rate can be obtained by a one-time amplification, thereby ensuring efficient enrichment of viral RNA and providing guarantee for subsequent reverse transcription and PCR amplification.

12 Claims, 7 Drawing Sheets

Specification includes a Sequence Listing.

The CT value of ORF/N gene detected by an extracting solution of "Wenzhou Medical University" is lower than that of "ZJ Bio-Tech Co., Ltd."

+ Anchor Primer

| | RNASE1 | RNASE2 | RNASE3 | RNASE4 | RNASE5 | RNASE6 | RNASE7 |
|---|---|---|---|---|---|---|---|
| Random forest | 0.85* | 0.75 | 0.75 | 0.75 | 0.75 | 0.9* | 0.75 |
| SVM | 0.577 | 0.564 | 0.819* | 0.571 | 0.758 | 0.347 | 0.652 |

A

B

| | RNASE1 | RNASE2 | RNASE3 | RNASE4 | RNASE5 | RNASE6 | RNASE7 |
|---|---|---|---|---|---|---|---|
| Random Forest | 0.9* | 0.85 | 0.75 | 0.7 | 0.7 | 0.75 | 0.85* |
| SVM | 0.74 | 0.728 | 0.893* | 0.69 | 0.834 | 0.495 | 0.794 |

PROTECTION METHOD, PROTECTION SEQUENCE, COMPOSITION AND KIT FOR PREVENTING RNA DEGRADATION, AND USE THEREOF

RELATED APPLICATIONS

The present application is a National Phase entry of PCT Application No. PCT/CN2020/112399, filed Aug. 31, 2020, which claims priority to Chinese Patent Application No. 202010602226.4, filed Jun. 28, 2020, the disclosures of which are hereby incorporated by reference herein in their entirety.

TECHNICAL FIELD

The present invention relates to the technical field of in vitro nucleic acid detection, in particular to a protection method, protection sequence, composition and kit for preventing RNA degradation, and applications thereof.

REFERENCE TO AN ELECTRONIC SEQUENCE LISTING

The contents of the electronic sequence listing (Name: 2022 PROTECTION METHOD, PROTECTION SEQUENCE, COMPOSITION AND KIT FOR PREVENTING RNA DEGRADATION, AND USE THEREOF; Sequence Listing XML; Date of Creation: Dec. 27, 2022; Size: 8,000 bytes) is herein incorporated by reference in its entirety.

BACKGROUND OF THE INVENTION

Ribonucleic acid (RNA), a genetic information carrier present in biological cells and some viruses and viroids, has only single strands, is unstable, and is easily degraded by RNase. RNase is very active, and abundant in nature. In order to prevent the degradation of RNA by RNase and improve the yield of target RNA during experiments or tests, it is of great significance to research and develop various RNA extraction techniques and methods.

SUMMARY OF THE INVENTION

In order to solve the problems existing in the prior art, the present invention provides a protection method, protection sequence, composition and kit for preventing RNA degradation, and applications thereof, which further improve a protection effect on virus RNA.

The technical solutions employed in the present invention are summarized as follows: a protection method for preventing RNA degradation includes the following step: forming an RNA:DNA complex by efficient binding of a RNase protection sequence (RNase-AP) to target RNA, wherein such binding reduces an exposure area of RNA, so that RNase cannot effectively cleave the target RNA and prevent RNA degradation.

A binding position of the RNase protection sequence (RNase-AP) to the target RNA is an RNase recognition site on the target RNA.

A protection method for preventing RNA degradation includes the following step: forming a complex by binding of a RNase protection sequence (RNase-AP) to RNase, wherein the complex affects the activity of RNase, inhibits the ability of binding the RNase to the target RNA, and prevents the target RNA from being degraded.

A binding position of the RNase protection sequence (RNase-AP) to the RNase is an RNase recognition site on the RNase.

A protection method for RNA degradation includes the following step: binding a RNase protection sequence (RNase-AP) to target RNA to cause local structure changes in the target RNA, such that the efficiency of binding the RNase to the target RNA is reduced or the binding position is changed, and RNase cannot cleave and degrade the target RNA, preventing the target RNA from being degraded.

A binding position of the RNase protection sequence (RNase-AP) to the target RNA is an RNase recognition site on the target RNA.

An RNase protection sequence uses a sequence of a RNase recognition site as the RNase protection sequence.

An RNase protection sequence is applied in the preparation of a virus detection reagent.

A virus detection composition includes the RNase protection sequence.

A virus detection kit includes the virus detection reagent.

The present invention has the following beneficial effect: the present invention provides a protection method, protection sequence, composition and kit for preventing RNA degradation, and applications thereof, which further improve a protection effect on virus RNA. After the definite addition of the RNase AP protection sequence, a three-dimensional structure of the target protected RNA and the structural allosteric characteristics of RNA can achieve a better protection effect on RNA integrity, and a high detection rate can be obtained by one-time amplification, ensuring efficient enrichment of virus RNA and providing guarantee for subsequent reverse transcription and PCR amplification.

DETAILED DESCRIPTION OF THE INVENTION

The experimental methods used in the following examples are conventional methods unless otherwise specified.

The SARS-CoV-2 novel coronavirus is now used, and the effect is further verified by the protection method against RNA degradation described in the present invention:

(I) Effective Recognition of SARS-CoV-2 Virus and Protection Effect and Mechanism of Novel Sample Treatment Solution on Virus RNA.

Primer sequences of new RNA protection sites are designed for a target gene of the novel coronavirus.

In addition, a composition ratio, a compound reagent concentration, a salt ion concentration, PH, etc. of various components for lysis/protection in a sample treatment solution are optimized, and a novel lysis solution reaction system (II) Optimization on Specificity of Primers/Probes: The Specificity of the Kit is Improved, the False Positive Rate is Effectively Reduced, and the Detection Rate is Increased; and with Reference to the Structure of the Novel Coronavirus, Novel Specific Primers/Probes are Designed to Cope with Possible Mutations of the Current Virus.

By designing a probe with dual gene targets of ORFlablab and N genes against the SARS-CoV-2 virus and performing simultaneous detection, the specificity of the detection of targeted cancer RNA is achieved. The primer design to other regions of ORFlab is added to realize the detection of multiple genes and sites, and effectively increase the detection rate of the kit. Meanwhile, the homology of different types of coronaviruses is analyzed in detail, combined with the latest research results of the 2019 novel coronavirus in structural biology and bioinformatics, to cope with the possible mutations of the 2019 novel coronavirus against a new primer probe designed for its highly conserved region, thereby realizing the immediate update of the detection kit, and ensuring the detection accuracy.

Figure 8A:
FIG. 8A shows design of protection sequence for N gene coordinates 28548-28763.
Figure 8A:
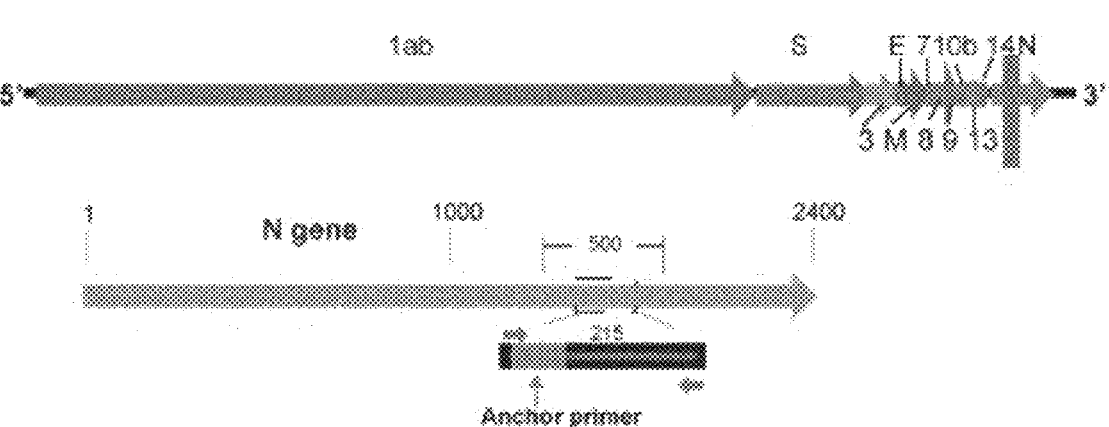
Figure 9A:
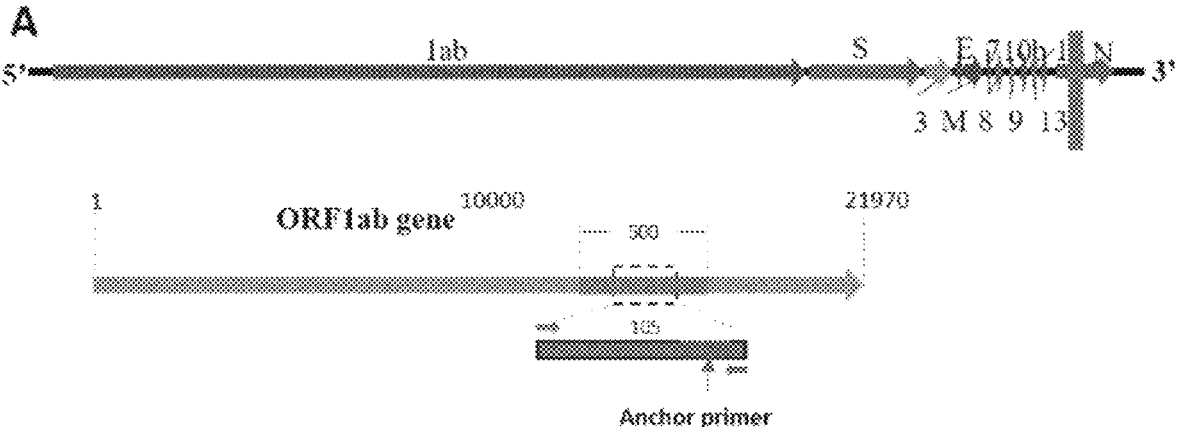
FIG. 9A shows design of protection sequence for ORFlab gene coordinates 2889-2997.

Through bioinformatic analysis, we first designed specific protection sequences for N gene (gene coordinates 28548-28763, FIG. 8A) and ORFlablab gene (gene coordinates 2889-2997, FIG. 9A) of SARS-COV-2, see AP-WHORFlab-1 and AP-WHN-1 in Table 1.

TABLE 1

| Name | Gene coordinates | Detected fragment size (nt) | Protection primer sequence | Sequence ID No. |
|------|------------------|-----------------------------|----------------------------|-----------------|
| ORFlablab | 2889-2997 | 105 | AP-WHORFlab-1:<br>gtcctcactgccgtcttgttgaccaacagtttgttgact | SEQ ID NO: 2 |
| N | 28548-28763 | 215 | AP-WHN-1:<br>cctcttctcgttcctcatcacgtagtcgcaacagttcaa | SEQ ID NO: 1 | is completed to further improve the protection effect of the lysis/protection solution on virus RNA. After the definite addition of an effective protection agent, a three-dimensional structure of a target protected virus RNA and the structural allosteric properties of the virus RNA are clarified, and the effective recognition of SARS-CoV-2 virus and the protection effect and mechanism of the sample treatment solution in this project kit on virus RNA are studied.

1. The composition ratio of the sample treatment solution is: 1 mmol/L 2-(N-morpholine) ethanesulfonic acid, 100 mmol/L NaCl, 100 mmol/L KCl, 10 mmol/L Tris-HCl, 5 mol/L guanidine hydrochloride, 1% Triton X-100, 0.1 mg/ml proteinase K, and 0.1 mg/ml kieselguhr, as well as 20 nM of a specially designed N gene protection sequence 1 (anchor primer, AP, protection sequence information is detailed in Part II, AP-WHN-1) and 20 nM of a specifically designed ORFlablab protection sequence (AP-WHORF1ab-1, protection sequence information is detailed in Part II).

2. Mechanism of action: first, AP binds to SARS-CoV-2 virus RNA to cause local structural changes in virus RNA, so that the efficiency of binding of RNase to virus RNA is reduced or the binding position is changed, and RNase cannot cleave and degrade virus RNA. Secondly, RNase-AP first binds efficiently to virus SARS-CoV-2 virus RNA to form a RNA: DNA complex, and such competitive binding reduces RNA exposure areas and prevents RNases from being effectively cleaved. Finally, RNase-AP may bind to RNAase to form a complex, and such binding competition inhibits the ability to bind to virus RNA and affects the RNase activity.

Figure 1:
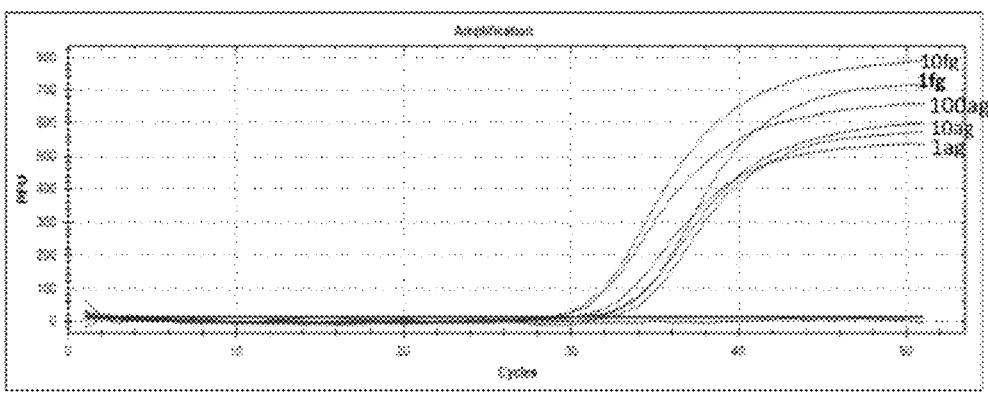
FIG. 1 shows the fluorescence quantitative detection of plasmid cDNA at different concentrations, with a minimum detection copy number of 1 ag (15 copies)/µl.

1. Bioinformatic structure prediction of SARS-CoV-2 virus RNA after binding of RNA to RNase-AP (FIGS. 8B and 9B), and prediction study of binding of SARS-CoV-2 virus RNA to RNase (FIGS. 1C and 2C) are performed.

1) First, we call RPIseq random forest and support vector machine algorithms to evaluate the binding characteristics of the protection sequence to human RNase. By scoring the affinity of RNase RNASE1-7 and a core sequence of N gene (ORFlab gene), it is found that RNASE1, RNASE3, and RNASE7 have a strong binding probability to the core sequence of N gene (ORFlab gene), which may serve as their potential target. catRAPID is called to predict a possible binding position of RNASE1-7 to the core sequence of N gene (ORFlab gene), and it is found that the protection sequence position can interact with RNase.

Figure 8B:
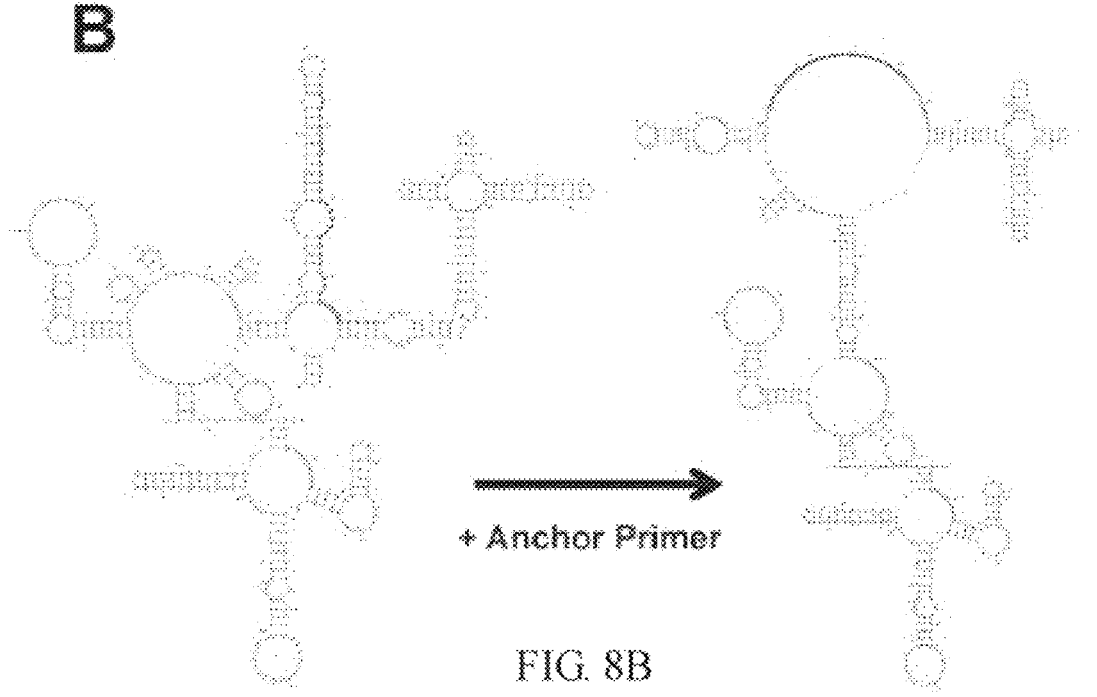
FIG. 8B is a schematic diagram of a secondary structure of a 500 nt fragment of N gene before and after AP binding.
Figure 9B:
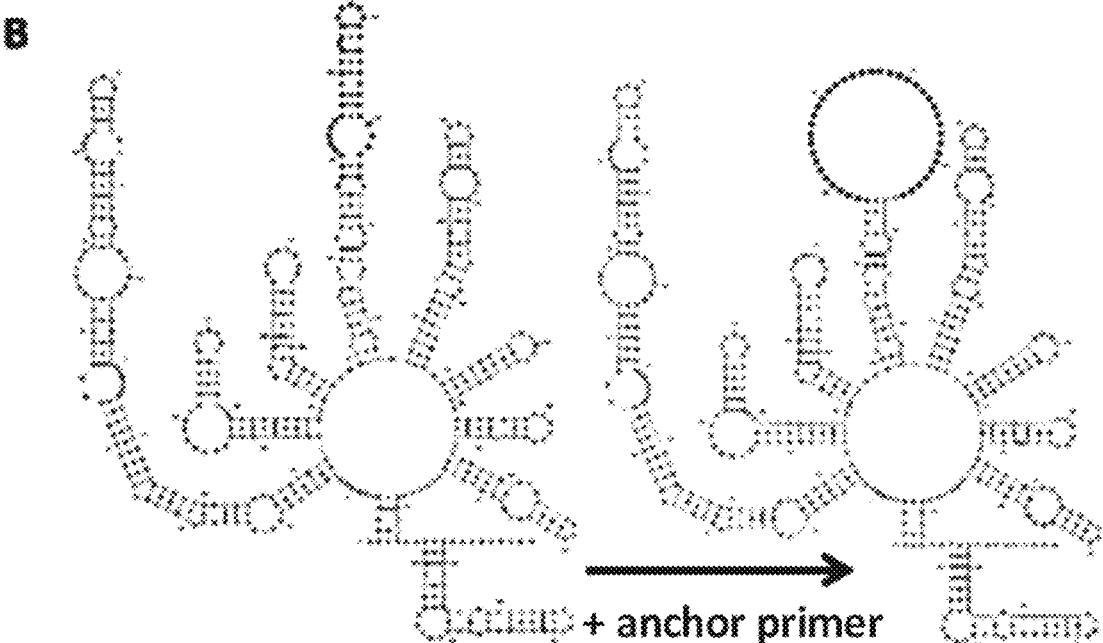
FIG. 9B is a schematic diagram of a secondary structure of a 500 nt fragment of ORFlab gene before and after AP binding.

Further, a minimum free energy prediction algorithm and RNAstructure are used to predict the RNA secondary structure before and after the binding of the protection sequence to the core sequence of N gene (ORFlab gene) of the virus, respectively. Further, a local alignment algorithm RNAsmc for the RNA secondary structure is used to compare the structural similarity. The results show that the core sequence of N gene (ORFlab gene) RNA before and after the binding to the protection sequence has a structural similarity score of 7.70 (on a scale of 1-10) for N gene and of 9.12 for ORFlab gene, which indicates that the protection sequence has a great influence on the overall structural state of the core sequence of N gene (ORFlab gene). To further validate the effect of primers on N gene (ORFlab gene), a PSMAliven structure alignment tool is used to quantify the effects of the binding region on the RNA structure of the core sequence of N gene (ORFlab gene) (FIGS. 8B and 9B). A PSMAlign result score of 0 indicates no change in structure, on the contrary, the higher the score, the more significant the difference. After calculation, the structural similarity of the core sequence RNA of N gene before and after the binding to the protection sequence is scored as 148 for N gene (18 for ORFlab gene), which indicates that the protection sequence has a great influence on the structure of N gene. In addition, this result is consistent with an evaluation result on RNAsmc, and the structural changes of the core sequence RNA of N gene (ORFlab gene) may cause abnormal molecular interaction.

Figure 8C:
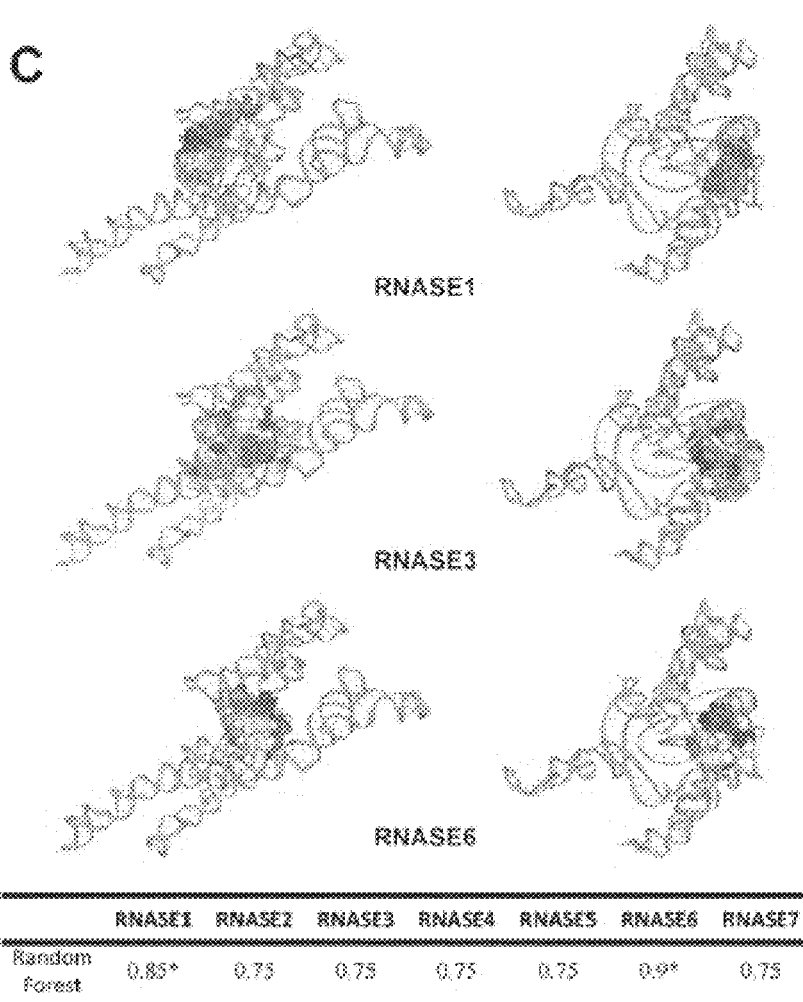
FIG. 8C shows predicted interaction regions of RNASE 1-7 and the core sequence of N gene.
Figure 9C:
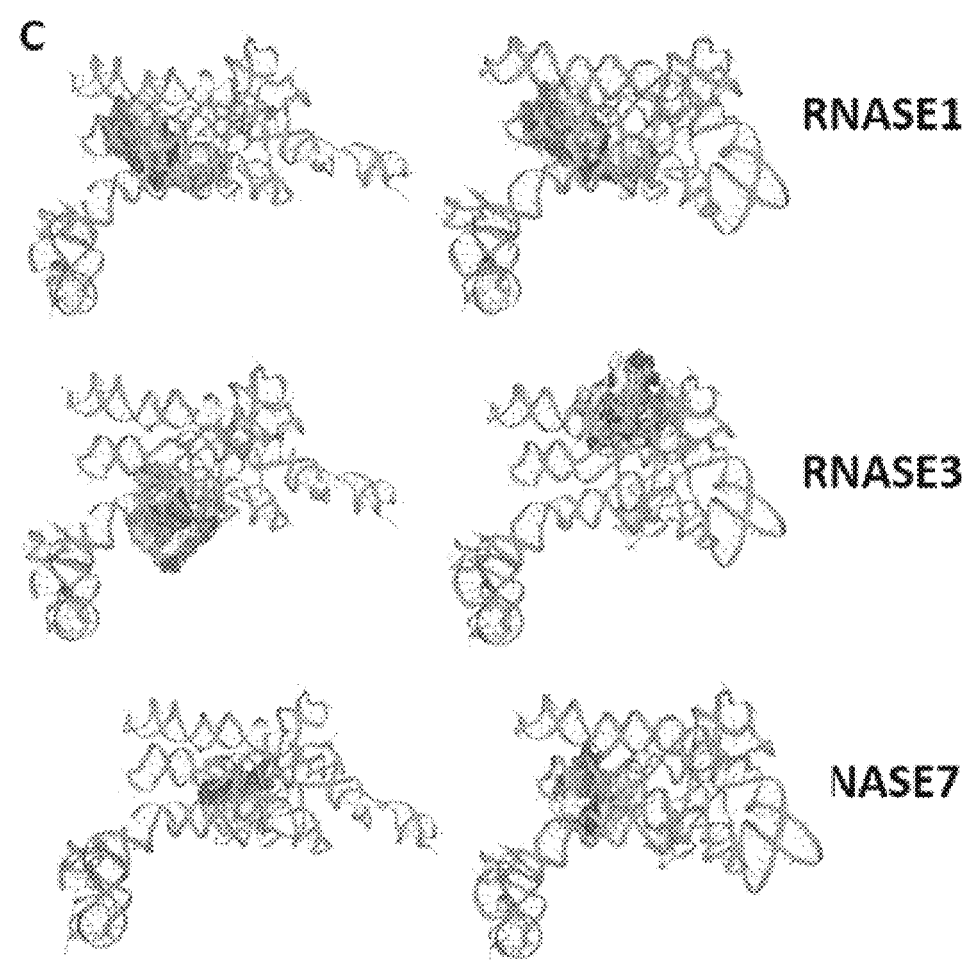
FIG. 9C shows predicted interaction regions of RNASE 1-7 and the core sequence of ORFlab gene.

2) RNAComposer is further used to predict a 3D structure of the core region of N gene (ORFlab gene), and HDOCK SERVER is used to predict an interaction region of RNase RNASE1-7 and the core sequence of N gene (ORFlab gene) (FIGS. 8C and 9C). The results show that the optimal interaction position of the core sequence of N gene (ORFlab gene) and RNase changes significantly after binding to the protection sequence, which further indicates that the structural changes of the core sequence RNA of N gene (ORFlab gene) may cause abnormal molecular interaction. The results show that RNase 1-7 has a strong probability of binding to the core region of N gene (ORFlab gene), can bind to N gene (ORFlab gene) at the protection sequence, and has a greater impact on the structure of N gene (ORFlab gene) after binding of the protection sequence to N gene (ORFlab gene). In addition, the optimal interaction position of the core sequence of N gene (ORFlab gene) and RNase changes significantly, which indicates that the structural changes of the core sequence RNA of N gene (ORFlab gene) may cause abnormal molecular interaction.

(III) SARS-CoV-2 Virus is Inactivated by Using the Sample Treatment Solution of the Kit, which is Developed into a Novel Virus RNA Preservation Solution by Studying the Components and Proportioning Process of the Sample Treatment Solution in the Kit; and its Biosafety of the Sample Treatment Solution in Clinical Testing is Investigated.

By improving the compatibility of the sample treatment solution of the kit with the kit, the virus is directly inactivated using a specific reagent, and the effects of its minimum and optimal concentrations on the detection sensitivity and specificity of the kit are investigated. The advantages and disadvantages between the sample treatment solution of this kit and the current RNA preservation solution, e.g., in terms of a preservation time, preservation conditions and preservation effects are compared and analyzed. It is proposed to use the sample treatment solution of this kit for the preservation of clinical pest specimens (viruses, bacteria, etc.), and its inactivation effect on the virus must be clarified. For the 2019 novel coronavirus, the virus inactivation effects are achieved by incubating at 60° C. for 5, 10, 20, and 30 minutes under different temperature conditions, thereby avoiding infection problems of detection personnel.

The sample treatment solution of this kit contains 5 mol/L guanidine hydrochloride, which can destroy the structure of a glycosylated coat protein of SARS-CoV-2 virus at room temperature and has an inactivation effect on SARS-CoV-2 virus. This kit has no degradation effect on standard RNA when standard RNA is incubated at 60° C. for 5, 10, 20, and 30 minutes. In addition, this kit has found in clinical tests that RNA of SARS-CoV-2 virus can still be extracted after 30 minutes of incubation at 60° C. In this way, this kit has a dual inactivation effect of guanidine salt and 60° C. warm bath (the Guidelines of the National Health Commission has specified that SARS-CoV-2 virus can be inactivated at 56° C. for 30 min).

By adding SARS-CoV-2 virus plasmid DNA and virus RNA standard to saliva, this kit has a minimum detection sensitivity of 15 copies/ml (cDNA) and 80 copies/ml (RNA standard; the clinical kit has a minimum detection sensitivity of −500 copies/ml at present) respectively, and has higher detection sensitivity.

The test results of this kit in 252 clinically confirmed COVID-19 positive cases show that the kit from Wenzhou Medical University has a better protection effect on RNA integrity under the action of AP of a single gene (N gene), and a high detection rate (80%) can be obtained by means of one-time amplification.

This kit detects the interference of common flora (including *Streptococcus pneumoniae, Streptococcus pyogenes, Klebsiella pneumoniae, Candida albicans, Staphylococcus aureus, Haemophilus influenzae* and *Aspergillus fumigatus*) on a detection system. It is found that common bacteria have no interference effect on the detection of SARS-CoV-2 virus RNA.

(4) The Protection Effect of Virus RNA is Improved and the Detection of Complex Samples is Achieved.

The sample treatment solution of this kit can be used to treat a variety of samples, increase the ability of the sample treatment solution to virus lysis and virus RNA release in complex samples, and improve the protection effect on virus RNA. Meanwhile, the adaptation conditions of this kit are optimized, the corresponding components in a washing solution are improved to effectively remove the interference of other components in complex samples, and the efficient enrichment of virus RNA is ensured to provide guarantee for subsequent reverse transcription and PCR amplification.

1. This kit can be used to treat a variety of SARS-CoV-2 samples, such as nasal swabs, pharyngeal swabs, sputum, urine, feces, conjunctival sac swabs and tears. It is founded in clinical testing:

| | Site 1 | Site 2 | Site 3 |
|---|---|---|---|
| Total cases | 57 | 115 | 75 |
| Age | 4-79 (52.74) | 1-93 (44.90) | 1-85 (39.74) |
| Sex | Male 31 (54.39%) | Male 58 (50.43%) | Male 38 (50.66%) |
| | Female 26 (45.61%) | Female 57 (49.57%) | Female 37 (49.33%) |
| Specimen type | Sputum 37 (64.91%) | Sputum 38 (33.04%) | Nasal swabs 22 (29.33%) |
| | Pharyngeal swab 10 (17.54%) | Pharyngeal swab 18 (15.65%) | Sputum 11 (14.67%) |
| | Feces 7 (12.28%) | Feces 15 (13.04%) | Pharyngeal 41 (54.67%) |
| | Nasal swab 3 (5.26%) | Sputum/pharyngeal 44 (38.26%) | unknown 1 (1.33%) |
| Detection rate | 70.18% | 80.87% | 78.67% |
| Mean CT value | 31.72 | 27.75 | 32.27 |

2. Treatment of special samples:

1) Feces: picking a small amount of sample and put it in the sample treatment solution, incubating at 60° C. for 30 minutes, centrifuging at 12000 rpm for 1 minute, and putting the supernatant onto the column for extraction. This kit can inactivate the virus on the one hand at this step; and effectively lyse the virus to release SARS-CoV-2 virus RNA on the other hand, and AP in the sample treatment solution immediately exerts its protection role.

2) Urine: first, centrifuging a collected clinical urine specimen, centrifuging at 12000 rpm for 2 minutes, taking 200-300 ul of urine from the lower layer, and adding 500 ul of sample treatment solution. This step will further concentrate epithelial cells in the urine and degrade all for sample treatment. This step is critical for handling abnormalities in small amount of samples.

(5) Primers and Probes of the Kit.

This kit sets a specific protection region for the protection sequence region, SARS-CoV-2.

| N protection sequence | cctcttctcgttcctcatcacgtagtc gcaacagttcaa | SEQ ID NO: 1 |
|---|---|---|
| WHN1-F2 sequence | 5 to CAAGCCTCTTCTCGTTCCT-3' CAAGCCTCTTCTCGTTCCT | SEQ ID NO: 3 |
| WHN1-R2 sequence | 5'-GCAGCAGATTTCTTAGTGACAG-3' GCAGCAGATTTCTTAGTGACAG | SEQ ID NO: 4 |

-continued

| N-probe sequence | 5'-FAM-ATTCAACTCCAGGCAGCAGT AG-BHQ1-3' ATTCAACTCCAGGCAGCAGTAG | SEQ ID NO: 7 |
|---|---|---|
| ORF1ab protection sequence | gtcctcactgccgtcttgttgacca acagtttgttgact | SEQ ID NO: 2 |
| WHO1-F2 sequence | 5'-GCCACTTCTGCTGCTCTTC-3' GCCACTTCTGCTGCTCTTC | SEQ ID NO: 5 |
| WHO1-R2 sequence | 5'-tgattgtcctcactgccgtc-3' tgattgtcctcactgccgtc | SEQ ID NO: 6 |
| ORF1ab probe sequence | 5'-VIC-CAACCTGAAGAAGAGCAA GAA-MGB-3' CAACCTGAAGAAGAGCAAGAA | SEQ ID NO: 8 |

Detection Steps:

1. Preparation before the experiment: it is necessary to ensure that experimental facilities are available, and the temperature of a metal bath and a water bath must be calibrated and verified.

2. Sample treatment

| 1. Sample treatment* | Treating the sample with a sample treatment solution (about 800 μl) containing a sample at 60° C. for 10 min, putting a supernatant onto a column, centrifuging at 12000 rpm for 30 s, and discarding effluent |
|---|---|
| 2. Rinsing | Adding 60 μl of rinsing solution, centrifuging at 12000 rpm for 30 s, and discarding effluent Adding 400 μl of rinsing solution, centrifuging at 12000 rpm for 45 s, discarding effluent, and then performing air centrifugation for 2 min to remove residual ethanol |
| 3. Elution** | Transferring the adsorption column to a new 1.5 ml centrifuge tube, adding 45 μl of eluent, performing heat preservation at 60° C. for 3 min, and centrifuging at 12000 rpm for 2 min. |
| 4. Reverse transcription | Taking 8 μl of eluted sample solution after centrifugation, adding 7 μl of NP reaction solution, and reacting at 42° C. for 10 min |
| 5. PCR amplification | Adding 15 μl of PCR reaction solution and putting on the machine |

Negative control: ddH$_2$O;

Positive control: 3 μl (full-length plasmid of N gene);

Steps 4 and 5 are performed according to the above treatment procedures.

*Feces specimens need to be centrifuged at 12000 rpm for 1 min, and the supernatant is taken and incubated at 60° C. for 10 min for subsequent experiments.

**Eluant should be treated in a warm bath at 60° C. for 10-15 minutes before use.

3. PCR amplification

The following procedure is performed on a fluorescent quantitative PCR instrument: setting of cyclic parameters (please refer to instrument operating instructions for setting)

| | Steps | Temperature | Time | Number of cycles |
|---|---|---|---|---|
| 1 | Pre-denaturating | 95° C. | 3 min | 1 |
| 2 | Denaturating | 95° C. | 10 s | 45 cycles |
| | Annealing | 58° C. | 35 s | |

In step 2, fluorescence detection is performed at 58° C. to determine whether fluorophore FAM and quenching group MGB exist, and ROX correction is not selected if there is no MGB option.
*The principle of threshold setting is that a threshold line exceeds a highest point of the negative control and is at the beginning of the exponential amplification period of the positive control.

Quality Control

The quality control procedure is to monitor the detection of negative control and positive control at the same time. The detection result is valid if the negative and positive control results comply with the cases specified by the interpretation of test results.

Interpretation of Test Results:

Negative (−): no Ct value or Ct value≥45

Positive (+): Ct value≤40.

To be reviewed: 40<Ct value<45, and a positive result is determined if Ct value <45 after review again.

(1) Inactivation of Virus Samples

The high-precision novel coronavirus (SARS-Cov-2) detection kit is based on a development technology of a predecessor cancer early detection kit (RNA detection), and the biosafety risk of collected samples has been technically optimized and improved in the early stage; and on this basis, the compatibility of existing technologies in pharyngeal swabs, nasal secretions and feces has been studied. A reagent is used to treat the sample with guanidine salt, the virus is inactivated after the sample is incubated at 600° C. for 30 minutes, and the subsequent study will shorten the time to 10 minutes.

(2) Detection Stability of Kit

By effectively identifying multiple sites and forming complexes in RNA samples released by cleavage, a triple PCR or multiplex PCR method is used to simultaneously detect multiple gene fragments such as an open reading frame and N gene of coronavirus (SARS-Cov-2) to avoid the existence of false negative caused by virus mutation. The recognition of RNA sequences in multiple sites protects the RNA integrity, avoids RNA degradation problems caused by sample treatment, and solves the problem of false positive through the optimization of primers and probes, so that the system can determine positive detected at any gene locus of novel coronavirus as positive for initial screening. Multi-target genes are used for protection, and a plurality of gene sequences is detected while the mutation of the virus needs to be considered, thereby preventing missed detection caused by mutation.

Easy degradation of RNA: this kit has released RNA into the sample treatment solution at the same time as the sample acquisition, the sample treatment solution can protect the RNA integrity very effectively while efficiently identifying the released RNA sample at multiple sites and forming complexes, and effective RNA protection is also designed in subsequent detection operations and verified in multiple developed products.

Sensitivity and specificity of the kit: during sample treatment, the RNA sample has been specifically and effectively identified at multiple target gene loci to form a compound, which stably targets novel coronavirus RNA, and multi-target RNA amplification is achieved by selective reverse transcription and enrichment of specific RNA complex; the self-designed primers and probes are significantly superior to probe and primer sequences published by the National Center for Disease Control (bioinformatic analysis has found that no secondary structure such as a hairpin-like structure exists); and by designing primers and probes for dual gene targets of the ORF1ab and N genes and detecting both sites at the same time, the sensitivity and specificity of the kit will be greatly improved.

The present invention has the following advantages.

(1) A unique reaction system of innovative lysate and kit: the sample treatment solution can directly store collected virus samples, the sample treatment solution containing guanidine salt which can effectively and rapidly inactivate the virus. At the same time, self-designed materials may also be added to the sample treatment solution, a three-dimensional structure of the target protected RNA and the structural allosteric properties of RNA make the target gene specifically recognized and protected, thereby increasing the sensitivity and specificity of detection.

(2) A unique reaction system of the kit: the combined use of the innovative lysate and reagent makes this detection kit have four characteristics: high sensitivity (100 times higher than Shanghai "ZJ Bio-Tech Co., Ltd. (Liferiver)"), high specificity, high speed (40-45 minutes from sample preparation to results) and dual direct inactivation of the virus to avoid infection of detection personnel.

(3) Effective treatment of unique sample treatment solution for complex samples (feces and sputum): the sputum sample has been verified in the technology development, the treatment effect on the clinical sample is very satisfactory in the early stage of technology development, and a product, i.e., a lung cancer early detection kit (Guo Xie Zhu Zhun: 20173403247), has been developed using the reagent before optimization. We can apply the existing sample treatment method to clinical applications in samples such as feces.

(4) Rapid sample preparation to detection (40 minutes): the kit currently developed by our team includes four detection steps: release, identification (5 min)—washing (1 min)—elution (2 min)—signal amplification (35 min). Results can be obtained within 45 minutes for pharyngeal swab samples. If used with an automatic nucleic acid extractor, this time can be shortened to 40 minutes.

Conclusion:

(1) By adding COVID-19 virus plasmid DNA and virus RNA standard to saliva, this kit has a minimum detection sensitivity of 15 copies/ml (cDNA) and 80 copies/ml (RNA standard; the clinical kit has a minimum detection sensitivity of about 500 copies/ml at present) respectively.

(2) The detection results in clinical 252 COVID-19 positive cases show that the kit from Wenzhou Medical University has a better protection effect on RNA integrity (N gene locus), and a high detection rate (80%) can be obtained by means of one-time amplification.

(i) Taizhou Enze Medical Center (57 cases) (CT values need to be re-statistically analyzed): the CT value of ORF gene detected by the extracting solution from "Wenzhou Medical University" is significantly lower than that of an extracting solution from "ZJ Bio-Tech Co., Ltd.", and the detected CT value of ORF gene is decreased by an average of 2.27 cycles, indicating that the sensitivity is improved by about 10 times (p=0.0001 paired with t-test, n=33), while the sensitivities of N gene and E gene are also reduced (p=0.0074 and p=0.6894).

(ii) Wenzhou CDC (59 cases): the CT values of N and E genes detected by extracting solution+amplification solution from "Wenzhou Medical University" are significantly lower than those of other clinical kits (decreased by 3.74 cycles for N gene, p=0.0001; decreased by 2.0 cycles for E gene, p=0.002, n=59);

(ii) Zhejiang CDC (54 cases): the CT values of N and E genes detected by extracting solution+amplification solution from "Wenzhou Medical University" are significantly lower than those of other clinical kits (decreased by 3.79 cycles for N gene, p<0.0001; decreased by XX cycles for E gene, p=0.002, n=59);

(iv) the 1$^{st}$ Affiliated Hospital and 2nd Affiliated Hospital of Wenzhou Medical University (54 mild cases): these cases are detected out by extracting solution from "Wenzhou Medical University"+amplification solution from "ZJ Bio-Tech Co., Ltd.", including 4 cases, accounting for 7.4% (4/54), which become positive again after turning negative;

(v) the 1st Affiliated Hospital of Wenzhou Medical University (11 cases): the detection rate from urine is 36.36% (4/11);

(vi) the positive rate of COVID-19 (N gene) detected by this kit at one time: 70.18% (40/57) in Taizhou; 80.87% (97/115) in Wenzhou CDC: N gene; and 78.67% (59/75) in Zhejiang CDC: N gene. The 2$^{nd}$ Affiliated Hospital of Wenzhou Medical University: 54 cases of clinical mild/ordinary type (turning positive in convalescent phase): 4 cases, 7.4% (4/54).

(3) Therefore, this kit can treat various types of specimens, such as nasal/pharyngeal swabs, sputum, saliva, feces and urine, etc., and trace virus specimens that may exist such as tears and conjunctival sac swabs are being verified.

A detailed progress report is as follows:

(1) Ethics: approved by the ethics committee of Eye Hospital of Wenzhou Medical University.

(2) The COVID-19 pseudovirus cDNA/RNA test indicates that the kit from Wenzhou Medical University has a minimum detection copy number of about 15 copies/ml (for cDNA standard) and 80 copies/ml (for RNA standard), showing higher sensitivity than that of the current clinical kit, and can detect lower viral titers in patient samples and effectively reduce the false negative rate.

2.1. Minimum detection copy number for COVID-19 pseudoviral plasmid cDNA: pseudoviral plasmid cDNA (provided by Xiamen Zeesan Biotech Co., Ltd.) is added to the simulated sample of sputum/saliva, and after the entire lysis/extraction and RT-PCR reaction steps, it is obtained that the minimum copy number of plasmid cDNA of this kit is about 1 ag (15 copies)/μl (FIG. 1) (the current clinical kit has the minimum copy number of about 500 copies/ml).

Figure 2:
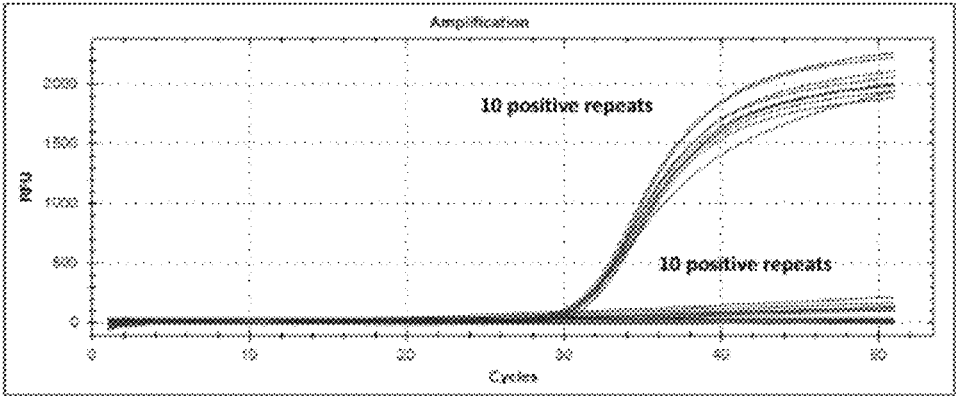
FIG. 2 shows the repeatability detected by virus cDNA: RT-PCR (15 copies/ml), with 10 replicates of 1 ag plasmid cDNA and 10 replicates of negative control, without any false positive in 50 cycles of Q-PCR amplification.

2.2. Repeatability of minimum copy number in detection of COVID-19 pseudoviral plasmid cDNA: pseudoviral plasmid DNA having a minimum detection copy number of 15 copies/ml (10 replicate tubes) is added to the simulated sample of sputum/saliva, and after the entire lysis/extraction and RT-PCR reaction steps, this kit has good repeatability in the case of the minimum copy number (FIG. 2).

Figure 3:
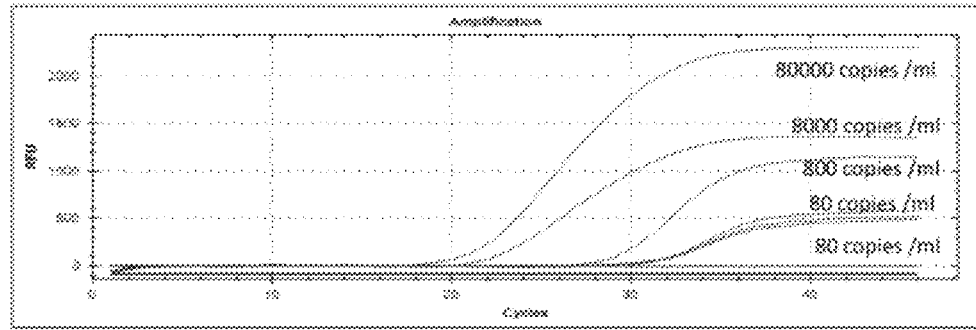
FIG. 3 shows that a minimum detection copy number of a virus RNA standard during RT-PCR detection is 80 copies/ml.
Figure 4:
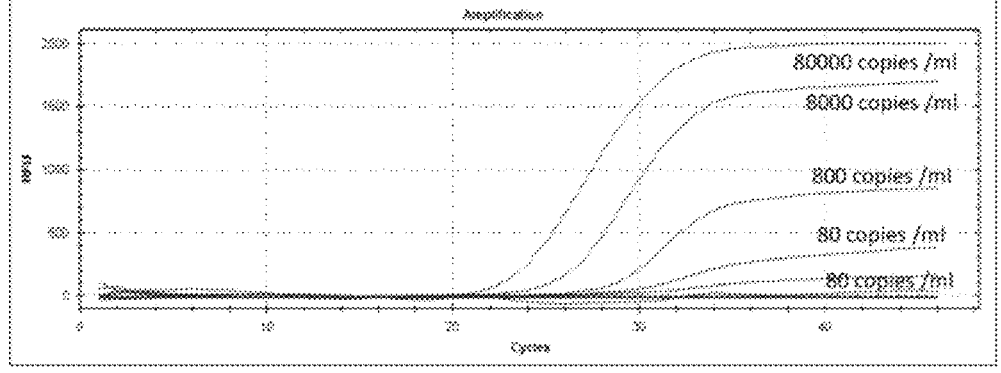
FIG. 4 shows that a minimum detection copy number of a simulated sample of saliva added with the virus RNA standard is 80 copies/ml.
Figure 5:
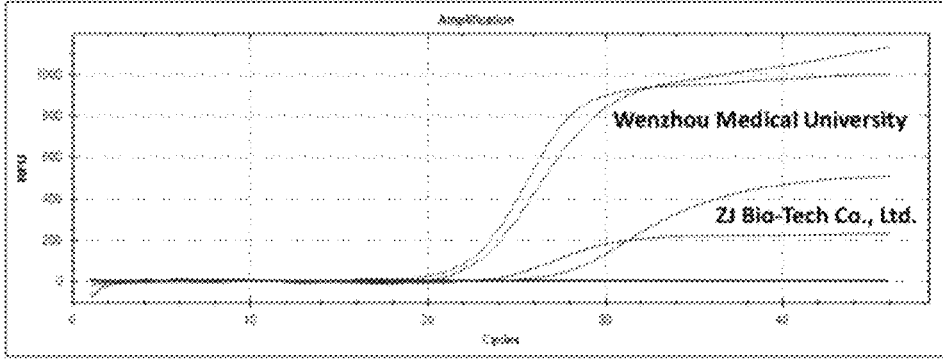
FIG. 5 shows the comparison of a detection effect of a commercial kit A and a detection effect of a commercial kit B as virus RNA standards in saliva samples.
Figure 6:
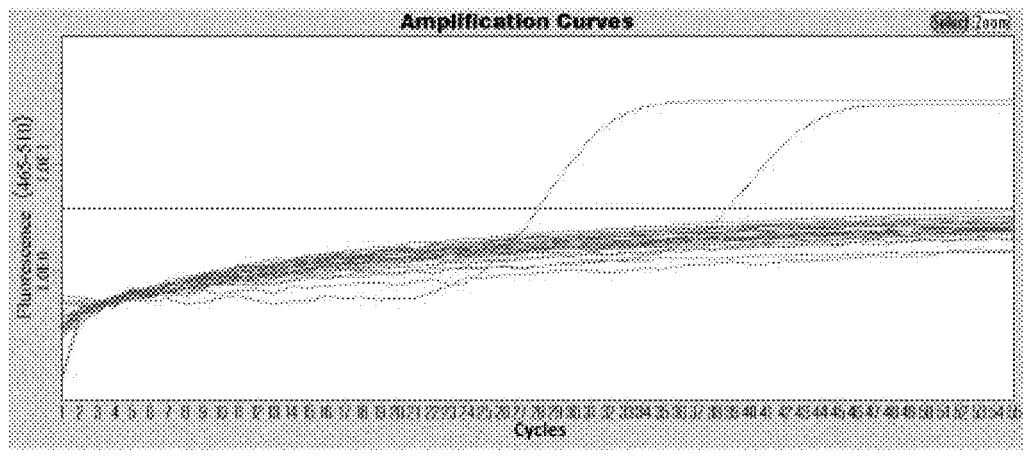
FIG. 6 shows that common bacteria have no interference effect on the detection of COVID-19 virus RNA.

2.3. Verification of the minimum detection copy number in the RT-PCR reaction step with COVID-19 virus RNA standard: the novel coronavirus RNA standard (provided by National Institute of Metrology, China) is added to the simulated samples of the RT-PCR reaction system (FIG. 3) and saliva (FIG. 4), to verify that the minimum detection copy number of the RT-PCR reaction step is 80 copies/ml (about 500 copies/ml for the current clinical kit).

2.4. Parallel comparison studies have found that: 8380 copies/ul of novel coronavirus RNA standard (provided by National Institute of Metrology, China) is added to the simulated sample of sputum/saliva, the RT-PCR reaction steps of the kits from "Wenzhou Medical University" and "ZJ Bio-Tech Co., Ltd." are compared, wherein the CT value detected in "Wenzhou Medical University" is 20, with high intensity of fluorescence signals; and the CT value detected in "ZJ Bio-Tech Co., Ltd." is 26, with low intensity of fluorescence signals.

2.5. Common bacteria have no interference effect on the detection of COVID-19 virus RNA The extracting solution (from Wenzhou Medical University)+RT-PCR amplification system (from ZJ Bio-Tech Co., Ltd.) is applied to detect the interference effects of common flora (including *Streptococcus pneumoniae, Streptococcus pyogenes, Klebsiella pneumoniae, Candida albicans, Staphylococcus aureus, Haemophilus influenzae* and *Aspergillus fumigatus*) on the detection system. The experimental results (3 replicates of nucleic acid extracted from bacteria) show that the expected amplification appears in the strong positive and weak controls (red), while interfering bacteria show no amplification (green).

(3) Statistics of clinical COVID-19 patient sample collection:

| Participating units | Pharyngeal swab | Nasal swab | Sputum/ saliva | Tear/conjunctival sac swab | Urine | Feces/anal swab | Negative | In total |
|---|---|---|---|---|---|---|---|---|
| 1$^{st}$ Affiliated Hospital of Wenzhou Medical University | 0 | 0 | | 43 | 20 | 10 | 0 | 84 |
| 2$^{nd}$ Affiliated Hospital of Wenzhou Medical University | 6 | 0 | 0 | 11 | 0 | 0 | 70 | 86 |
| Taizhou Enze Medical Center | 10 | 3 | 37 | 0 | 0 | 7 | 0 | 57 |

-continued

| Participating units | Pharyngeal swab | Nasal swab | Sputum/ saliva | Tear/conjunctival sac swab | Urine | Feces/anal swab | Negative | In total |
|---|---|---|---|---|---|---|---|---|
| Wenzhou Epidemic Disease Prevention and Control Center | 44 | 18 | 38 | 0 | | 15 | 0 | 58 |
| Zhejiang Epidemic Disease Prevention and Control Center | 41 | 22 | 11 | 0 | 0 | 0 | 0 | |
| Eye Hospital of Wenzhou Medical University | 0 | | 0 | 0 | 0 | 0 | 150 | 150 |

3.2. Study on the effects of lysis/protection solution from Wenzhou Medical University on stable protection of COVID-19 virus RNA In order to detect that the innovative lysis/protection solution can specifically and effectively identify multiple COVID-19 target gene loci and form complexes to stably protect COVID-19 virus RNA, the cooperative unit (Taizhou Enze Hospital) compares the RNA extracted from the lysis/protection solutions from the "Wenzhou Medical University" and "ZJ Bio-Tech Co., Ltd." kits in 33 positive specimens, and the nucleic acid detection kit from "ZJ Bio-Tech Co., Ltd." is used for RT-PCR amplification detection. The results of clinical experiments show that:

(1) The results of clinical experiments show that the positive rate of COVID-19N gene detection is 95%, the positive rate of E gene detection is 100%, and the positive rate of ORF/RDRP gene detection is 100%. This indicates that the kit has a better protection effect on RNA integrity (multiple gene loci) and enables the detection of multiple genes for one-time amplification to improve the detection rate and accuracy of the samples (Table 1).

| Inpatient/outpatient number | Gender | Age | Specimen type | Detection results | Extraction and detection from ZJ | Extraction and detection from WMU |
|---|---|---|---|---|---|---|
| 50151329 | Male | 56 | Sputum | Positive(+) | RDRP26.2932/E25.83/N26.29 | RDRP 25.79/E 25.85/N 26.7 |
| 50151142 | Male | 75 | Sputum | Positive(+) | RDRP35.21/34.45/34.91 | RDRP 37.35/E 0/N 39.57 |
| 50151377 | Female | 67 | Pharyngeal swab | Positive(+) | RDRP38.05/E37.48/39.02 | RDRP 35.74/E 37.03/N 34.96 |
| 50151088 | Male | 55 | Feces | Positive(+) | RDRP37.68/E37.09/N38.70 | RDRP 37.65/E 36.94/N 36.8 |
| 50151536 | Female | 77 | Nasopharyngeal swab | Positive(+) | rdrp33.3/E35/N33.07 | RDRP 28.11/E 29.25/N 27.32 |
| 50151345 | Male | 64 | Sputum | Positive(+) | rdrp32.9/E30.3/N38.6 | RDRP 32.87/E 32.7/N 31.86 |
| 50151329 | Male | 56 | Sputum | Positive(+) | RDRP30.38/E29.53/N30.21 | RDRP 29.47/E 29.12/N 28.46 |
| 50151379 | Male | 55 | Nasopharyngeal swab | Positive | RdRP38.97/E38.9/N37 | RDRP 0/E 39.71/N 37.71 |
| 50151118 | Female | 65 | Nasopharyngeal swab | Positive | RdRP 35.25/E 35.21/N 33.51 | RDRP 35.15/E 34.33/N 33.95 |
| 50151406 | Male | 33 | Sputum | Positive(+) | rdrp35.6/E34.6/N33.5 | RDRP 31.58/E 32.11/N 30.69 |
| 50150887 | Male | 34 | Sputum | Positive | RDRP33.9/E29.9/N 30.8 | RDRP 32.81/E 32.58/N 32.3 |

-continued

| Inpatient/outpatient number | Gender | Age | Specimen type | Detection results | Extraction and detection from ZJ | Extraction and detection from WMU |
|---|---|---|---|---|---|---|
| 50151409 | Female | 51 | Sputum | To be reviewed | E36, N35.9 | RDRP 0/E 36.29/N 43.69 |
| 50150812 | Male | 50 | Sputum | Positive(+) | rdrp37.4/E35.5/N35 | RDRP 35.07/E 34.2/N 33.9 |
| 50151541 | Female | 48 | Sputum | Positive(+) | rdrp36.99/E35.6/N35.6 | RDRP 0/E 0/N 35.14 |
| 50151270 | Female | 44 | Pharyngeal swab | Positive | RDRP 35.22/E31.68/N 32.97 | RDRP 35.15/E 32.35/N 31.75 |
| 50151536 | Female | 77 | Sputum | Positive(+) | RDRP29.8/E28.0/E29.2 | RDRP 21.43/E 22.17/N 23.09 |
| 50151307 | Female | 68 | Sputum | To be reviewed | E37.9/N38.7 | RDRP 31.38/E 31.94/N 31.83 |
| 50150765 | Female | 56 | Sputum | Positive(+) | RDRP35.6/E32.7/N33.3 | RDRP 35.26/E 34.32/N 33.9 |
| 50151436 | Female | 30 | Sputum | Positive(+) | RDRP37.46/E34.5/N36.36 | RDRP 35.25/E 34.54/N 34.06 |
| 50150798 | Male | 43 | Sputum | Positive(+) | rdrp36.34/E33.1/N33.03 | RDRP 37.03/E 34.43/N 35.89 |
| 50151142 | Male | 75 | Sputum | Positive(+) | RDRP38.66/E35.7/N37.5 | RDRP 38.95/E 39.82/N 28.03 |
| 50151345 | Male | 64 | Sputum | Positive(+) | rdrp34.91/E33.9/N32.53 | RDRP 37.08/E 37.22/N 36.98 |
| 9000548489 | Female | 43 | Pharyngeal swab | Negative | RdRP 41.7/E 36.56/N 36.9 | RDRP 35.91/E 35.84/N 36.04 |
| 50150798 | Male | 43 | Pharyngeal swab | Positive | RdRP38.30/E 38.14/N 35.78 | Non-standard curve |
| 50151020 | Female | 26 | Pharyngeal swab | Positive(+) | RdRP 38.79/E 37.07/N 37.71 | RDRP 33.87/E 34.02/N 34.27 |
| 50150887 | Male | 34 | Pharyngeal swab | Positive(+) | RdRP 31.61/E 28.56/N 28.78 | RDRP 28.86/E 28.92/N 28.44 |
| 50151237 | Male | 70 | Pharyngeal swab | Positive | RDRP38.01/E35.94/N35.38 | RDRP 33.6/E 35.07/N 34.09 |
| 50151166 | Male | 44 | Pharyngeal swab | Positive | RdRP 32.53/E 31.16/N 35.41 | RDRP 33.74/E 33.65/N 33.64 |
| 50151065 | Male | 51 | Sputum | Positive(+) | RDRP37.70/E37.12/N37.94 | RDRP 29.08/E 28.45/N 28.47 |
| 50150954 | Female | 41 | Pharyngeal swab | Positive | RdRP 33.77/E 32.98/N 39.01 | RDRP 32.3/E 32.56/N 32.68 |
| 50151017 | Male | 38 | Pharyngeal swab | Positive | RdRP 39.91/E 39.93/N 38.21 | Non-standard curve |
| 50151406 | Male | 33 | Faeces | Positive | RDRP33.12/E30.88/N32.29 | RDRP 23.98/E 25.39/N 24.04 |

-continued

| Inpatient/outpatient number | Gender | Age | Specimen type | Detection results | Extraction and detection from ZJ | Extraction and detection from WMU |
|---|---|---|---|---|---|---|
| 50151406 | Male | 33 | Sputum | Positive | RDRP35.53/E32.72/N34.12 | Non-standard curve |

Figure 7:
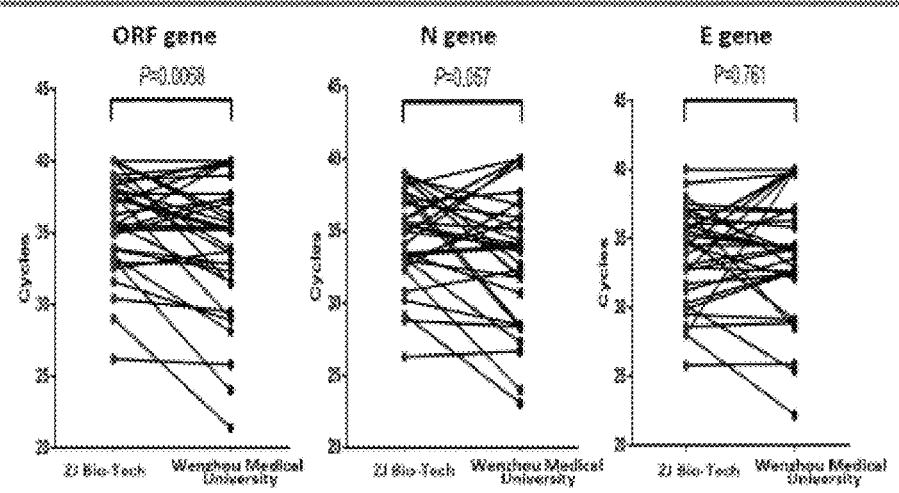
FIG. 7 shows that the CT value of ORF gene detected by an extracting solution of "Wenzhou Medical University" is lower than that of an extracting solution of the commercial extraction kit A.

(2) The CT values of three gene fragments (ORF, E and N) detected by the extracting solutions from "Wenzhou Medical University" and "ZJ Bio-Tech Co., Ltd." are compared. The results show that the CT value of the ORF gene detected by the extracting solution from "Wenzhou Medical University" is significantly lower than that of the extracting solution from "ZJ Bio-Tech Co., Ltd." ($p=0.0067$, N gene, $p=0.057$; E gene, $p=0.761$, paired with t-test, $n=33$, see FIG. 7), the CT value of the ORF gene is reduced by an average of 3 cycles, and the copy number of detected COVID-19RNA by pseudoviral standard curve conversion is increased by about 10 times.

3.4. Clinical compliance rate (vi) The positive rate of COVID-19 (N gene) detected by this kit at one time: 70.18% (40/57) in Taizhou; 80.87% (97/115) in Wenzhou CDC: N gene; and 78.67% (59/75) in Zhejiang CDC: N gene. The 1st Affiliated Hospital of Wenzhou Medical University: 54 cases of clinical mild/ordinary type (turning positive in convalescent phase): 4 cases, 7.4% (4/54).

3.5. The extracting solution from "Wenzhou Medical University" can treat a variety of complex COVID-19 patient samples:

can effectively reduce the exposure risk of detection personnel, protect the safety of operators, and reduce the risk of infection in testing laboratories.

3.7. Rapid Sample Preparation to Detection (40 Min):

This kit includes four detection steps: release, identification (5 min)—washing (1 min)—elution (2 min)—signal amplification (35 min). Results can be obtained within 45 minutes for pharyngeal swab samples. If used with an automatic nucleic acid extractor, this time can be shortened to 40 minutes.

3.8. Detection Sensitivity

By adding COVID-19 virus plasmid DNA and virus RNA standards, it is found in ex vivo experiments that this kit has the minimum detection sensitivities of 15 copies/ml (cDNA) and 80 copies/ml, respectively, with a low detection line. In addition, clinical detection in 1st Affiliated Hospital and 2nd Affiliated Hospital of Wenzhou Medical University has found that among 54 patients recovering from COVID-19, there are patients who are positive after turning negative clinically. Therefore, this kit has high detection sensitivity.

The materials, reagents, etc. used in the following examples unless otherwise specified, may be obtained commercially.

| Participating units | Pharyngeal swab | Nasal swab | Sputum/saliva | Tear/conjunctival sac swab | Urine | Feces/anal swab | Negative | In total |
|---|---|---|---|---|---|---|---|---|
| 1st Affiliated Hospital of Wenzhou Medical University | 0 | 0 | | 43 | 20 | 10 | 0 | 84 |
| 2nd Affiliated Hospital of Wenzhou Medical University | 6 | 0 | 0 | 11 | 0 | 0 | 70 | 86 |
| Taizhou Enze Medical Center | 10 | 3 | 37 | 0 | 0 | 7 | 0 | 57 |
| Wenzhou Epidemic Disease Prevention and Control Center | 44 | 18 | 38 | 0 | | 15 | 0 | 58 |
| Zhejiang Epidemic Disease Prevention and Control Center | 41 | 22 | 11 | 0 | 0 | 0 | 0 | |
| Eye Hospital of Wenzhou Medical University | 0 | | 0 | 0 | 0 | 0 | 150 | 150 |

3.6. COVID-19 Virus Inactivation and Safety

The sample treatment solution of this kit contains guanidine salt, which has an inactivation effect on the virus (which has been confirmed in existing reports). In addition, the sample treatment stage can achieve an effect of inactivation of the virus at 60° C. for 30 min. Virus inactivation Notes to technical personnel: although the present invention has been described in accordance with the above specific examples, the inventive idea of the present invention is not limited to the present invention, and any modification using the idea of the present invention will be included in the protection scope of this patent.

The above is only preferred examples of the present invention, the protection scope of the present invention is not limited to the above examples, all technical solutions belonging to the ideas of the present invention are within the protection scope of the present invention. It should be noted that those of ordinary skill in the art may also make several improvements and modifications without departing from the principles of the present invention, which should be considered as the protection scope of the present invention.

The invention claimed is:

1. A protection method for preventing RNA degradation, comprising the following step: forming an RNA: DNA complex by efficient binding of a SARS-Cov-2 viral RNase protection sequence to target RNA, wherein such binding reduces an exposure area of RNA, so that RNase cannot effectively cleave the target RNA and prevent RNA degradation, wherein the SARS-Cov-2 viral RNase protection sequence comprises the following nucleotide sequences:

```
                                          SEQ ID NO: 1
cctcttctcgttcctcatcacgtagtcgcaacagttcaa;
and
                                          SEQ ID NO: 2
gtcctcactgccgtcttgttgaccaacagtttgttgact.
```

2. The protection method for preventing RNA degradation according to claim 1, wherein a binding position of the SARS-Cov-2 viral RNase protection sequence to the target RNA is an RNase recognition site on the target RNA.

3. A protection method for preventing RNA degradation, comprising the following step: forming a complex by binding of a SARS-Cov-2 viral RNase protection sequence to RNase, wherein the complex affects the activity of RNase, inhibits the ability of binding the RNase to the target RNA, and prevents the target RNA from being degraded, wherein the SARS-Cov-2 viral RNase protection sequence comprises the following nucleotide sequences:

```
                                          SEQ ID NO: 1
cctcttctcgttcctcatcacgtagtcgcaacagttcaa;
and
                                          SEQ ID NO: 2
gtcctcactgccgtcttgttgaccaacagtttgttgact.
```

4. The protection method for preventing RNA degradation according to claim 3, wherein a binding position of the SARS-Cov-2 viral RNase protection sequence to the RNase is an RNase recognition site on the RNase.

5. A protection method for preventing RNA degradation, comprising the following step: binding a SARS-Cov-2 viral RNase protection sequence to target RNA to cause local structure changes in the target RNA, such that the efficiency of binding the RNase to the target RNA is reduced or the binding position is changed, and RNase cannot cleave and degrade the target RNA, preventing the target RNA from being degraded, wherein the SARS-Cov-2 viral RNase protection sequence comprises the following nucleotide sequences:

```
                                          SEQ ID NO: 1
cctcttctcgttcctcatcacgtagtcgcaacagttcaa;
and
                                          SEQ ID NO: 2
gtcctcactgccgtcttgttgaccaacagtttgttgact.
```

6. The protection method for preventing RNA degradation according to claim 5, wherein a binding position of the SARS-Cov-2 viral RNase protection sequence to the target RNA is an RNase recognition site on the target RNA.

7. A SARS-Cov-2 viral RNase protection sequence, which uses a sequence of a RNase recognition site as the RNase protection sequence, wherein the SARS-Cov-2 viral RNase protection sequence comprises the following nucleotide sequences:

```
                                          SEQ ID NO: 1
cctcttctcgttcctcatcacgtagtcgcaacagttcaa;
and
                                          SEQ ID NO: 2
gtcctcactgccgtcttgttgaccaacagtttgttgact.
```

8. Application A method of preparing a virus protection reagent, the method comprising
    combining a biological sample comprising target RNA
        with a treatment solution comprising the SARS-Cov-2
        viral RNase protection sequence according to claim 7.

9. A virus protection composition, comprising a salt solution of the SARS-Cov-2 viral RNase protection sequence according to claim 7.

10. A virus detection kit, comprising a fluorescent probe, primer sequences and the virus protection reagent according to claim 8.

11. The virus protection composition of claim 9 wherein the salt solution comprises guanidinium salt.

12. A virus detection kit comprising the virus protection reagent according to claim 8,

```
                              SEQ ID NO: 3
CAAGCCTCTTCTCGTTCCT,

SEQ ID NO: 4
GCAGCAGATTTCTTAGTGACAG,

SEQ ID NO: 5
GCCACTTCTGCTGCTCTTC,

SEQ ID NO: 6
TGATTGTCCTCACTGCCGTC,

SEQ ID NO: 7
ATTCAACTCCAGGCAGCAGTAG,
and

SEQ ID NO: 8
CAACCTGAAGAAGAGCAAGAA.

*   *   *   *   *
```

```
                          SEQUENCE LISTING

<160> NUMBER OF SEQ ID NOS: 8

<210> SEQ ID NO 1
<211> LENGTH: 39
<212> TYPE: DNA
<213> ORGANISM: Artificial Sequence
<220> FEATURE:
<223> OTHER INFORMATION: Synthesized N Protection Primer Sequence

<400> SEQUENCE: 1
cctcttctcg ttcctcatca cgtagtcgca acagttcaa                            39

<210> SEQ ID NO 2
<211> LENGTH: 39
<212> TYPE: DNA
<213> ORGANISM: Artificial Sequence
<220> FEATURE:
<223> OTHER INFORMATION: Synthesized ORF1ab1ab Protection Primer
      Sequence

<400> SEQUENCE: 2
gtcctcactg ccgtcttgtt gaccaacagt ttgttgact                            39

<210> SEQ ID NO 3
<211> LENGTH: 19
<212> TYPE: DNA
<213> ORGANISM: Artificial Sequence
<220> FEATURE:
<223> OTHER INFORMATION: Synthesized N Protection Sequence

<400> SEQUENCE: 3
caagcctctt ctcgttcct                                                  19

<210> SEQ ID NO 4
<211> LENGTH: 22
<212> TYPE: DNA
<213> ORGANISM: Artificial Sequence
<220> FEATURE:
<223> OTHER INFORMATION: Synthesized N Protection Sequence

<400> SEQUENCE: 4
gcagcagatt tcttagtgac ag                                              22

<210> SEQ ID NO 5
<211> LENGTH: 19
<212> TYPE: DNA
<213> ORGANISM: Artificial Sequence
<220> FEATURE:
<223> OTHER INFORMATION: Synthesized ORF1ab1ab Protection Sequence

<400> SEQUENCE: 5
gccacttctg ctgctcttc                                                  19

<210> SEQ ID NO 6
<211> LENGTH: 20
<212> TYPE: DNA
<213> ORGANISM: Artificial Sequence
<220> FEATURE:
<223> OTHER INFORMATION: Synthesized ORF1ab1ab Protection Sequence

<400> SEQUENCE: 6
```

```
tgattgtcct cactgccgtc                                          20

<210> SEQ ID NO 7
<211> LENGTH: 22
<212> TYPE: DNA
<213> ORGANISM: Artificial Sequence
<220> FEATURE:
<223> OTHER INFORMATION: Synthesized N Probe Sequence

<400> SEQUENCE: 7
attcaactcc aggcagcagt ag                                       22

<210> SEQ ID NO 8
<211> LENGTH: 21
<212> TYPE: DNA
<213> ORGANISM: Artificial Sequence
<220> FEATURE:
<223> OTHER INFORMATION: Synthesized ORF1ab1ab Probe Sequence

<400> SEQUENCE: 8
caacctgaag aagagcaaga a                                        21
```